United States Patent [19]
Mercereau

[11] Patent Number: 5,702,369
[45] Date of Patent: Dec. 30, 1997

[54] EXTENDABLE DEVICE FOR ENCLOSING CUTTING SURFACES OF SURGICAL INSTRUMENTS

[76] Inventor: Steven Frank Mercereau, 4911 W. Lake Dr., Conyers, Ga. 30208

[21] Appl. No.: 469,075

[22] Filed: Jun. 6, 1995

[51] Int. Cl.⁶ .................................. A61M 5/32; A61M 5/00
[52] U.S. Cl. .......................... 604/192; 604/110; 604/198; 604/263
[58] Field of Search .................. 604/110, 164–170, 604/192, 198, 263

[56] References Cited

U.S. PATENT DOCUMENTS

| | | | |
|---|---|---|---|
| 4,643,722 | 2/1987 | Smith, Jr. | 604/192 |
| 4,735,618 | 4/1988 | Hagen | 604/192 |
| 4,867,746 | 9/1989 | Dufresne | 604/192 |
| 4,994,041 | 2/1991 | Dombrowski et al. | 604/198 X |
| 5,026,356 | 6/1991 | Smith | 604/192 |
| 5,152,751 | 10/1992 | Kozlowski | 604/192 |
| 5,232,454 | 8/1993 | Hollister | 604/192 |
| 5,348,544 | 9/1994 | Sweeney et al. | 604/192 |
| 5,411,492 | 5/1995 | Sturman et al. | 604/263 |
| 5,466,223 | 11/1995 | Bressler et al. | 604/198 X |

*Primary Examiner*—Sam Rimell
*Assistant Examiner*—Robert V. Racunas
*Attorney, Agent, or Firm*—Kennedy, Davis & Kennedy

[57] ABSTRACT

A device attached to an end of a surgical cutting tool and extendable from a retracted position with a cutting surface of the tool exposed to an extended position with the cutting surface covered by the device to prevent inadvertent contacts with the cutting surfaces.

6 Claims, 7 Drawing Sheets

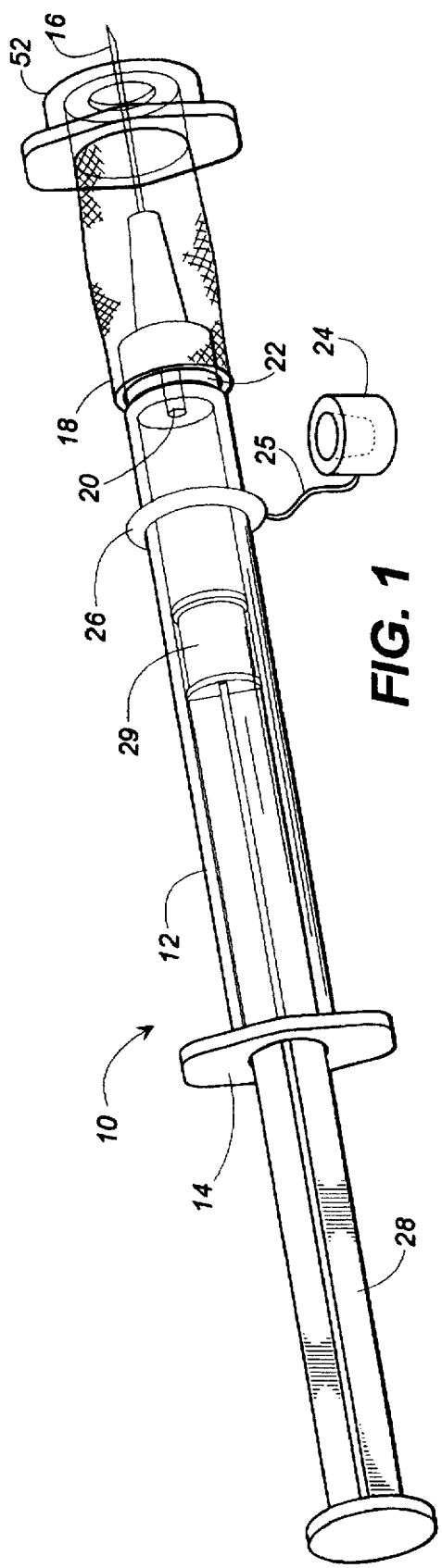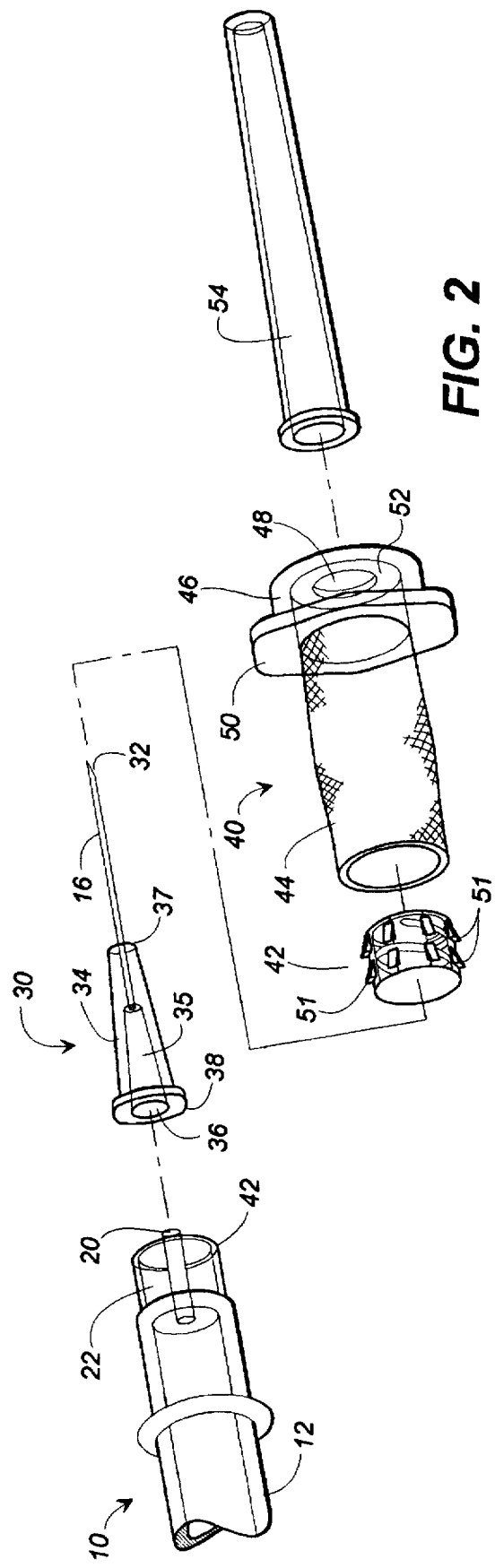

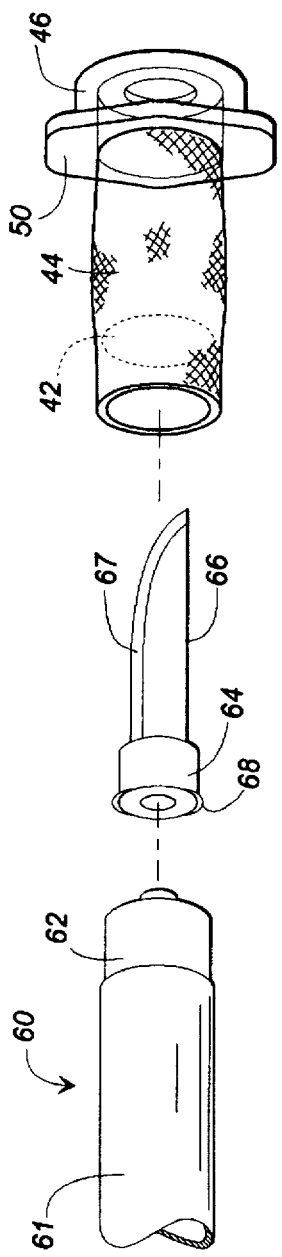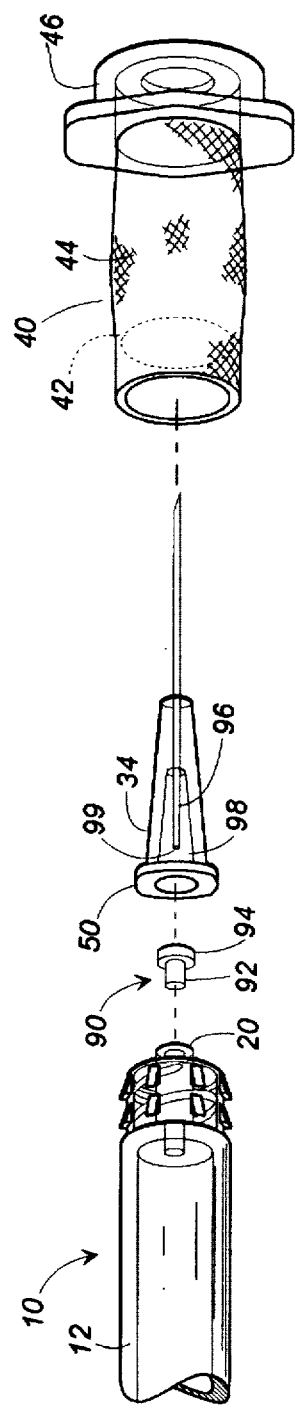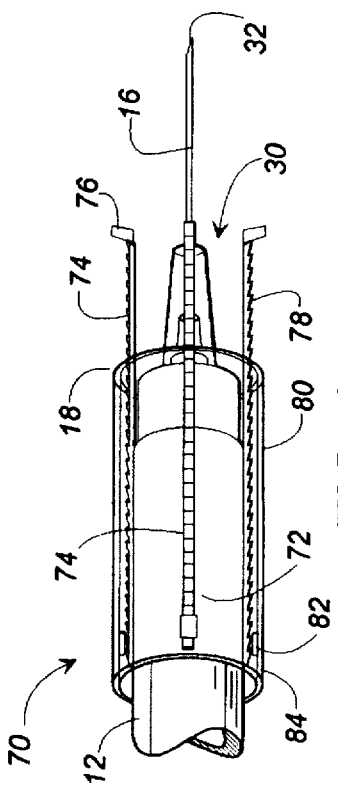

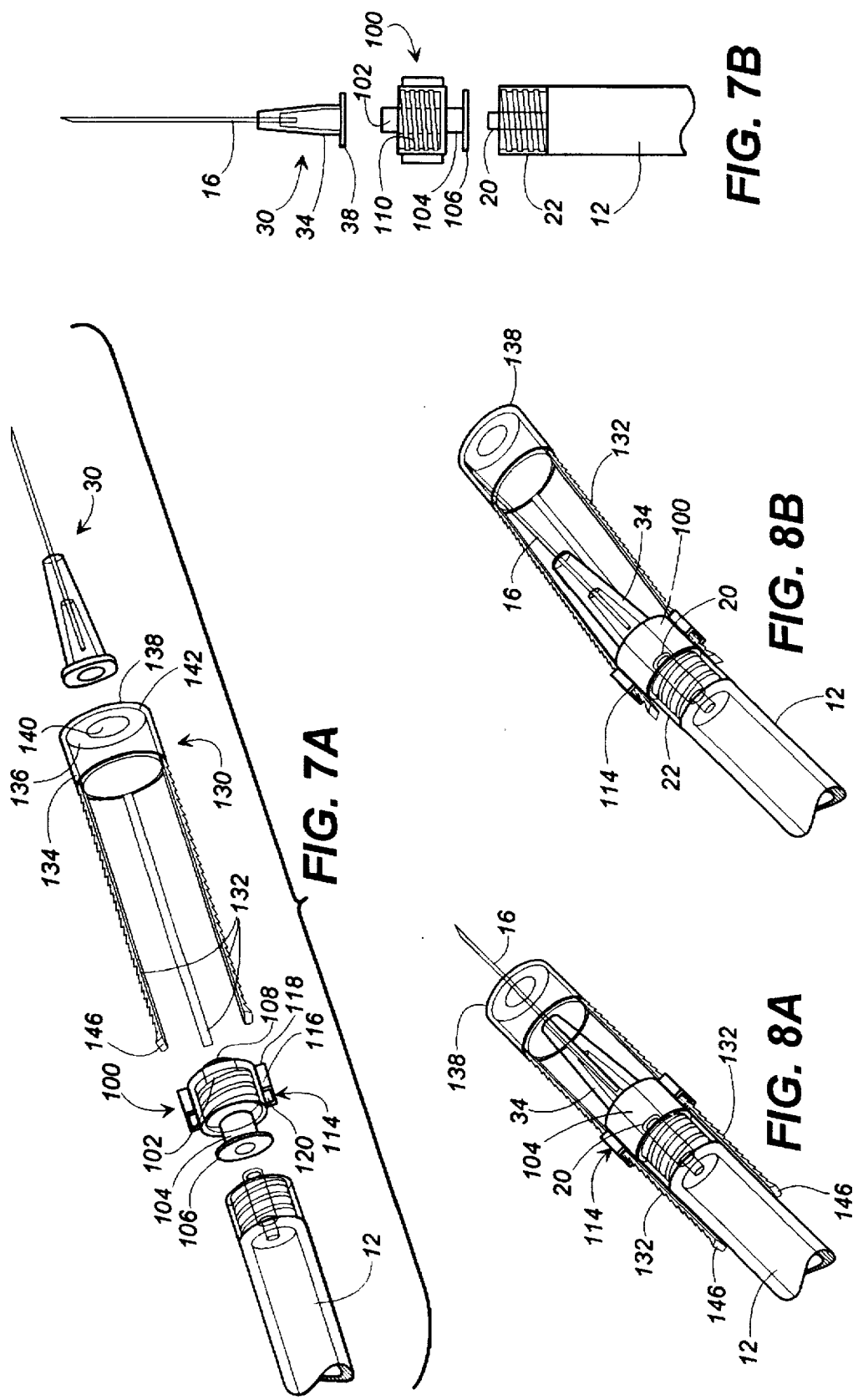

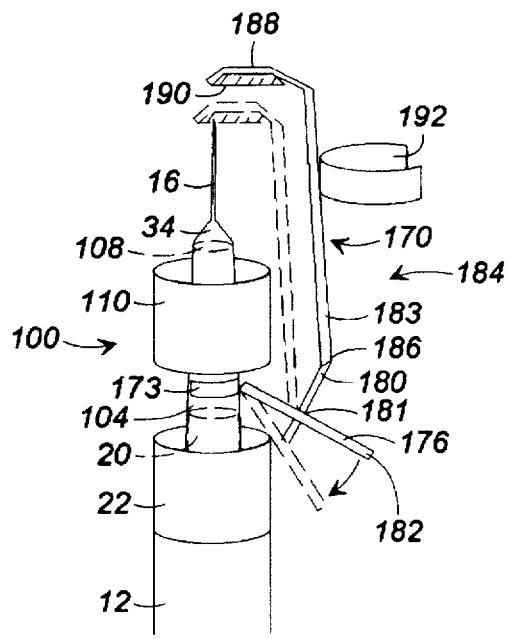
FIG. 9
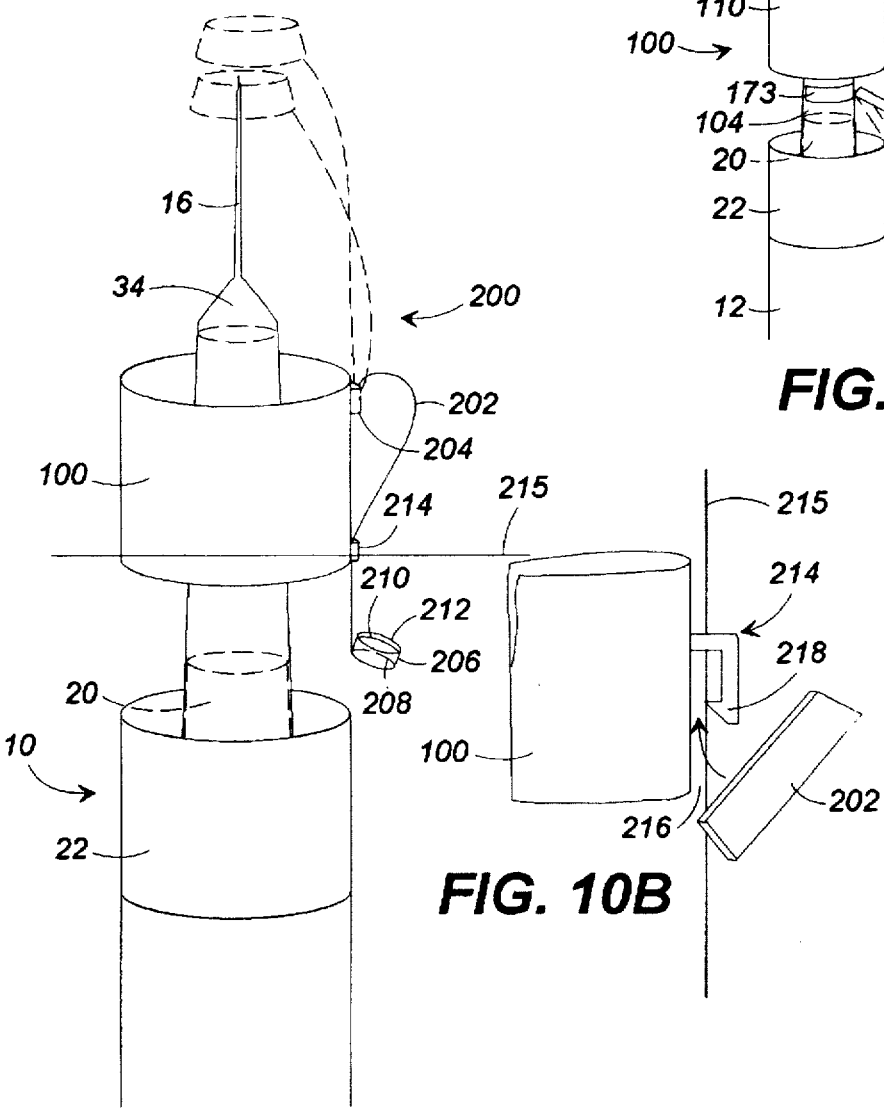
FIG. 10B
FIG. 10A

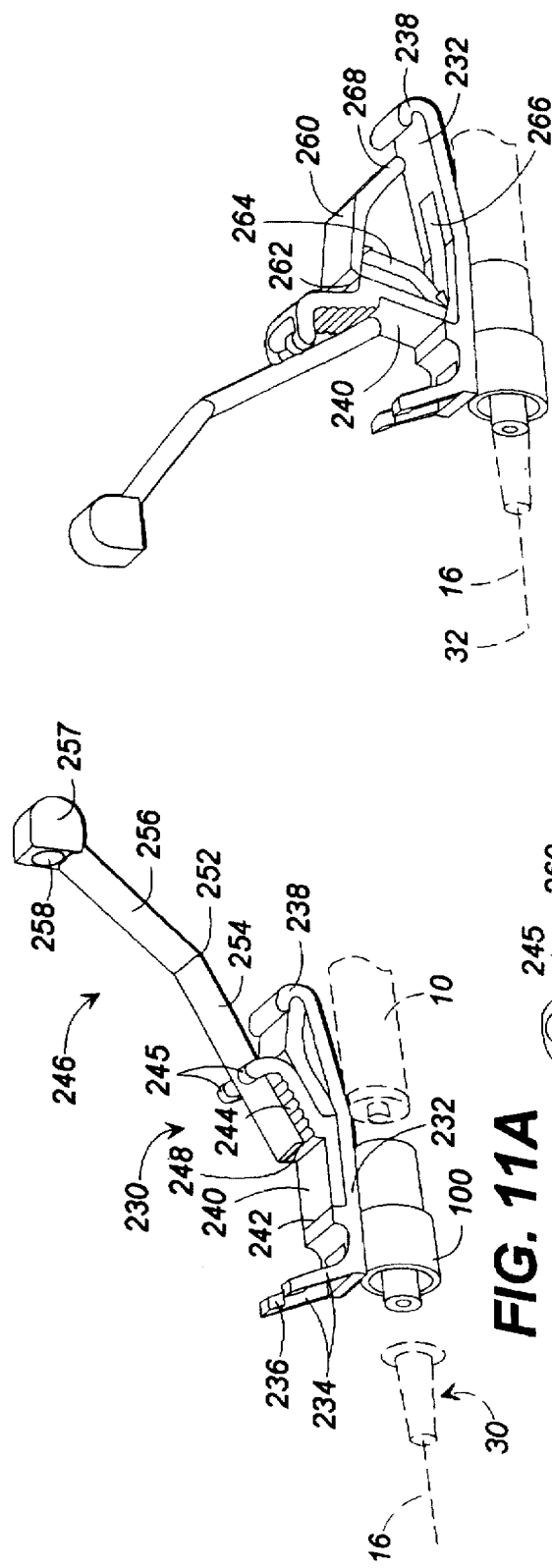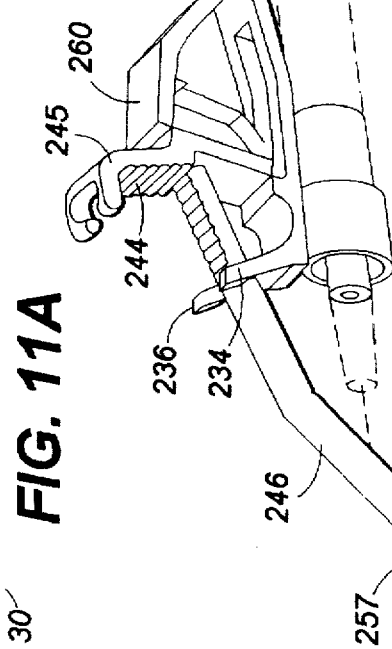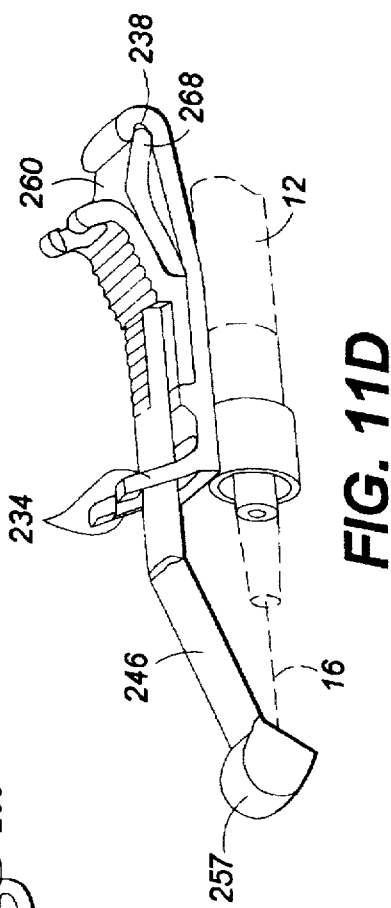
FIG. 11A
FIG. 11B
FIG. 11C
FIG. 11D

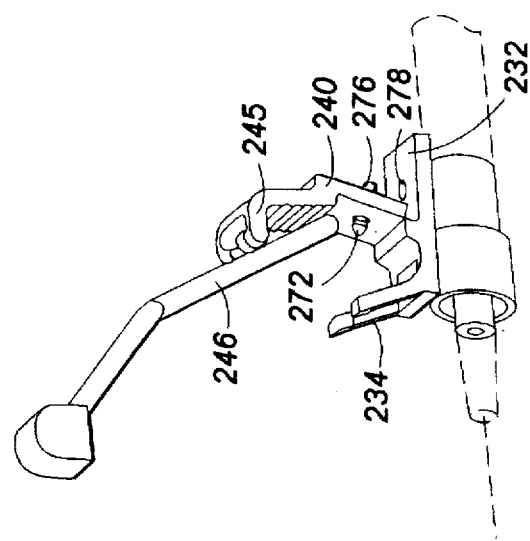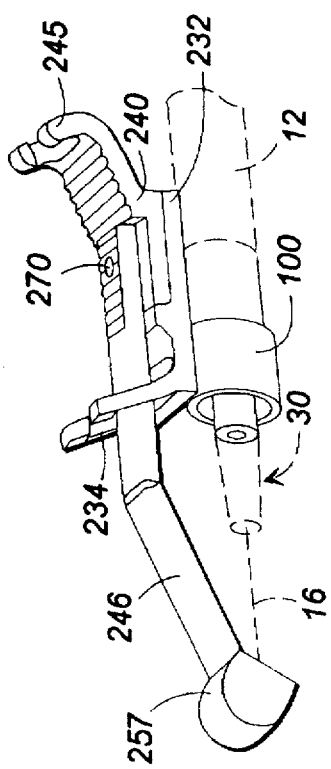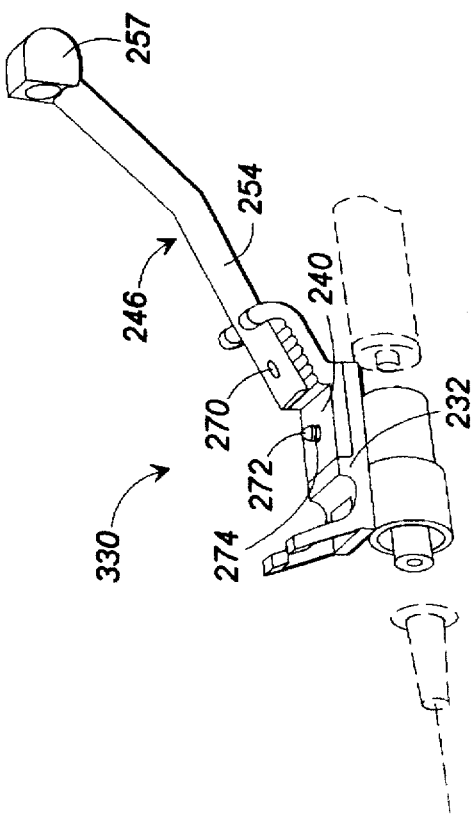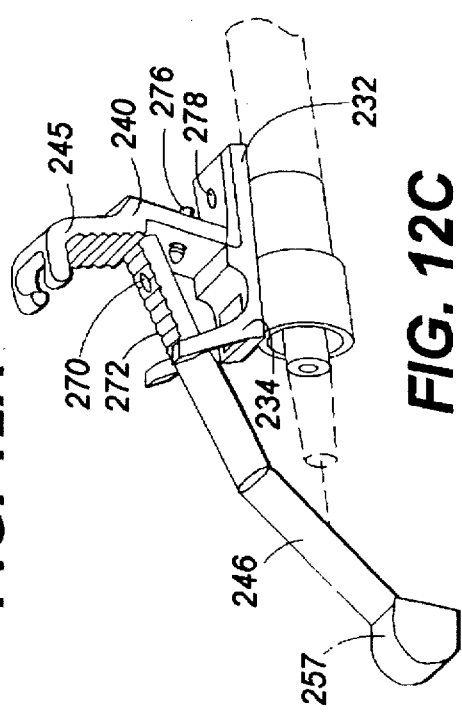

EXTENDABLE DEVICE FOR ENCLOSING CUTTING SURFACES OF SURGICAL INSTRUMENTS

TECHNICAL FIELD

The present invention relates to surgical instruments. More particularly, the present invention relates to extendable devices that enclose cutting surfaces of surgical instruments to prevent inadvertent contacts therewith.

BACKGROUND OF THE INVENTION

Surgical instruments having cutting surfaces are often used in medical procedures for patients. These instruments includes scalpels and syringes. Scalpels have knife-blade portions for cutting tissues; for example, to cut the skin for exposing portions of the patient for surgery. Syringes are commonly used both to inject medications into patients as well as to obtain samples of bodily fluids such as anaerobic blood samples. Syringes have needles with sharp tips, which communicate with a tubular barrel of the syringe for holding the medications or receiving the samples. After use, the scalpels and needles of the syringes are disposed of, typically by depositing in containers known in industry terms as "sharps containers", in reference to the sharp points and cutting surfaces of the tools placed inside. These sharps containers typically have one-way entrances for receiving surgical instruments for subsequent disposal in a sanitary disposal site. Surgical operating rooms and each of the patient rooms often have sharps containers for holding used surgical cutting tools.

Today there are substantial dangers associated with the handling and use of surgical instruments such as scalpels and syringes having bodily fluids. Care must be exercised during use and disposal of surgical instruments to avoid unintended contact with the cutting surfaces. For example, the syringe users sometimes prick themselves accidently while handling the syringe after the sample is drawn. One reason is that capping a needle is often difficult, particularly with one hand otherwise occupied. Where such occurs there is a possibility that a serious disease may be communicated from the patient's sample in the syringe to the nurse or other medical personnel using the syringe.

It is thus seen that a need remains for an improved device and method for shielding cutting surfaces of surgical instruments from inadvertent contact with persons after use of the instruments for their intended purposes. It is to the provision of such that the present invention is primarily directed.

SUMMARY OF THE INVENTION

In a preferred form of the invention, a capping device is provided for covering at least a tip end of a cutting surface means of a surgical instrument. The capping device comprises a cap attached to a member that is engaged to a surgical instrument having a cutting surface means. The member is selectively movable between a retracted position wherein the cap is remote from the cutting surface means, an extended position with the cap outwardly of at least a tip end of the cutting surface means, and an intermediate position in which at least the tip end of the cutting surface means is securely fixed to the cap. Means are provided for retaining the tip end fixedly in the cap.

In one embodiment, the present invention provides an enclosing device that mounts to a surgical instrument, such as a sampling syringe, for preventing inadvertent contact with cutting surfaces. A sampling syringe with the enclosing device comprises an elongated barrel open at a first end and a needle attached by a hub at a second end for communication with the barrel. A plunger rod with a plunger body attached at a first end is slidably insertable into the open first end of the barrel. The enclosing device comprises a sheath that attaches to the second end of the barrel and has a cup attached at a distal end of the sheath. The cup defines an opening for receiving the needle coaxially therethrough. The sheath is extendable between a retracted position in which the needle extends outwardly of the sheath and an extended position with the tip of the needle in contact with an interior surface of the cup.

The present invention also provides a method of securing a tip end of a needle attached to a sampling syringe by extending a sheath, biased for a retracted position near a first end of sampling syringe, coaxially along a needle that projecting outwardly of an opening in a cap attached to a distal end of the sheath. The sheath is moved to an extended position with the cap displaced outwardly of a tip end of the needle whereby the tip end is within the extended sheath. The distal end of the sheath is then moved laterally relative to the tip end of the needle, whereby the tip end is brought near an interior surface of the sheath. The distal end of the sheath is retracted slightly from its extended position to an intermediate position with the tip end of the needle being engaged by an interior surface of the cap for securing the tip of the needle.

The present invention also provides a device for enclosing a cutting surface of a surgical tool in order to restrict inadvertent contact with the cutting surface after use of the surgical tool. The device comprises an elongated handle having mount means at a first end for holding a member that includes a cutting surface. A plurality of arms extend coaxially from the first end of the handle and are preferably equally spaced apart circumfrentially around the handle. Each arm includes an outward surface that defines a series of spaced-apart grooves and a stop at a distal end. A slidable tube is received on the handle. Bearing blocks on the interior of the tube are associated with the arms and each includes a tongue that extends towards the handle at an acute angle relative to the first end for engagement with the grooves. The tube is movable between a retracted position with the member exposed and an extended position with the tube enclosing the member. The tongues engaged in the slots secure the tube in the extended position.

The present invention also provides a sampling syringe with an extendable device for capping a needle attached to the syringe. The syringe comprises an elongated barrel open at a first end and a needle attached by a hub to an intermediate connector at a second end for communication with the barrel. The intermediate connector has at least one pair of spaced-apart U-shaped bands attached to an exterior surface. A plunger rod with a plunger body attached at a first end slidably inserts into the open first end of the barrel. A device for capping a tip of the needle attaches to an elongate arm that is slidingly received between the bands and the exterior surface for guiding the travel of the arm relative to the tip of the needle. The arm has a series of stops therein for being received sequentially in the gap between the bands for securing the device in a selected position relative the tip of the needle. The arm moves between a retracted position in which the needle extends outwardly of an opening in the closing device and an extended position with the closing device outwardly of the tip of the needle. The closing device is movable laterally and slightly retracted for engaging the tip with an interior surface of the device.

The present invention provides a method of capping a needle attached to a sampling syringe with an extendable device. The steps of the method comprise inserting an arm through a pair of spaced-apart U-shaped bands attached to an exterior surface of an intermediate connector that is threadingly received on a barrel of a sampling syringe. A closing device attaches at a distal end of the arm which includes a series of stops therein for being received sequentially in a gap between the bands for securing the device in a selected position relative the tip of the needle. The arm is moved relative the tip of the needle from the retracted position with the needle extending outwardly through an opening in the closure device to an extended position with the closing device outwardly of the tip of the needle. The arm is then moved laterally relative to an axis defined by the needle to bring the tip of the needle adjacent an interior surface of the closure device. Finally, the arm is retracted to engage the tip of the needle with the closure device. The needle and the closure device are removable as a unitary member by detaching the intermediate member from the barrel.

The present invention also provides a sampling syringe with a closure device for capping a needle attached to the syringe. The closure device comprises a ring sized for being engaged to a tubular portion of a hub that holds the needle. A lever hingedly attaches to the ring and a link member hingedly connects to the lever intermediate the ring and a distal end of the lever. An arm connects by a flexible hinge to the link and has a dish-shaped cap member at a distal end. The arm is pivotable to a position in substantial parallel alignment with the needle whereby the cap member is outwardly of the tip of the needle. The cap member is then brought into engagement with the tip of the needle by moving the lever away from the needle.

The present invention also provides a capping device for covering a tip end of a cutting surface of a surgical instrument. The capping device comprises an elastic elongate member attached to the surgical instrument and having a cap attached at a distal end. A retaining block spaced apart from the attachment of the elongate member releasably retains the elongate member in a retracted position away from the cutting surface means. Upon release, the elongate member springs away from the retaining block to an extended position outwardly of a tip end of the cutting surface means. The member is thereafter movable to an intermediate position in which the tip end is fixedly received in the cap.

The present invention provides a needle enclosing device for capping a tip of a syringe needle after use. The device comprises a plate having a pair of spaced-apart guide posts that extend laterally at a first end of the plate which attaches to a sampling syringe. A lever arm pivotally connects at a first end to an upper surface of the plate away from the guide posts and a distal end of the lever arm has a pair of spaced-apart fingers that extend laterally therefrom. The lever arm pivots between a back position and a forward position. Art elongate arm pivotally connects at a first end to an upper surface of the lever arm between the connection to the plate and the distal end of the lever arm. A distal end of the elongated arm includes a cap for receiving a tip end of a needle in fluidal communication with a barrel of the sampling syringe. The elongate arm pivots from a retracted position with the arm held between the fingers and an extended position with the arm held between the guide posts. Means are provided for releasably securing the lever arm in the back position. The elongate arm, being released from between the fingers, pivots from the retracted position to the extended position while the lever arm is moved from the back position to the forward position to dispose the cap outwardly of the tip of the needle. The lever arm is then moved to the back position, which causes the elongate arm to move to an intermediate position for engaging the tip of the needle in the cap.

The lever arm is held in the back position by a distal end of a locking plate that engages a U-shaped hook in the plate. The lever arm in another embodiment is held by a peg that engages a bore in the plate. A second peg on the plate engages a bore in the elongate arm to hold the arm in the extended position.

BRIEF DESCRIPTION OF THE DRAWINGS

FIG. 1 is a side perspective view of a syringe enclosing device that embodies principles of the invention in a preferred form.

FIG. 2 is an exploded view of the syringe enclosing device of FIG. 1 for illustrating details thereof.

FIG. 4 is an exploded perspective view of a surgical instrument to which the enclosing device is mounted.

FIG. 5 is a perspective view of a syringe having an alternate embodiment of an enclosing device.

FIG. 6 is a perspective view of a syringe enclosing device attached to a syringe that includes a luer cap.

FIG. 7A is an exploded prospective view of a syringe that includes an alternate embodiment of the enclosing device of the present invention with an intermediate member.

FIG. 7B is an exploded side plan view of the intermediate member illustrated in FIG. 7A.

FIGS. 8A and 8B are prospective views of the syringe illustrated in FIG. 7, showing a sequence of relative positions of the closure device as used during an enclosing operation in accordance with the method of the present invention.

FIG. 9 is a prospective view of an alternate embodiment of a needle protection device for use on syringes according to the present invention.

FIG. 10A is a perspective view of an alternate embodiment of a needle protection device for use on syringes according to the present invention.

FIG. 10B is a side elevational view of a retaining block used with the needle protection device shown in FIG. 10A.

FIG. 11A-11D are perspective views of a needle protection device according to the present invention, illustrating the device in a retracted, extended, and intermediate positions for shielding a syringe needle.

FIG. 12A-12D are perspective views of an alternate embodiment of the needle protection device illustrated in FIG. 11A.

DETAILED DESCRIPTION

Figure 3A:
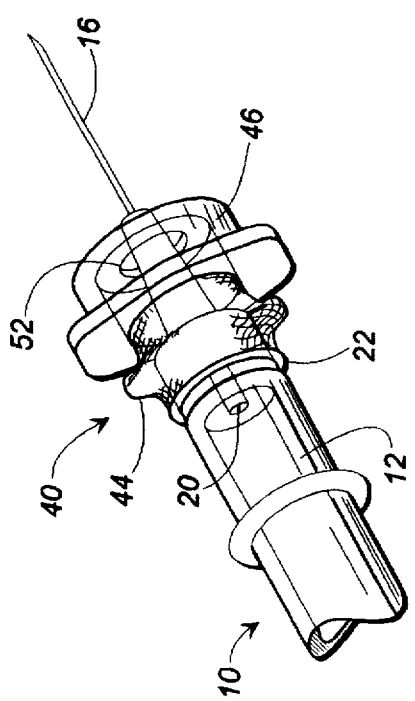
FIGS. 3A-3D are perspective views of a syringe with the enclosing device mounted thereto, which show a sequence of relative positions of the enclosing device with respect to the syringe as it is used during an enclosing operation in accordance with a method of the invention.

Referring now in more detail to the drawings, in which like numerals indicate like parts throughout the several views, FIGS. 1 and 2 show a sampling syringe 10 that comprises an elongated tubular barrel 12 open at one end 14 and with a hypodermic needle 16 attached at the other end 18 for communication with the barrel. A luer 20 extends outwardly axially from the end 18 and defines an narrow tubular connector for receiving a needle assembly, as discussed below. A shroud 22 coaxially surrounds a lower portion of the luer 20. The shroud 22 is spaced radially from an exterior surface of the luer 20 and defines a well between the luer, the shroud, and an end surface at the end 18 of the barrel. In a preferred embodiment, an interior surface of the shroud 22 includes a thread for engaging a needle assembly 30 that holds the needle 16 as discussed below. In the illustrated embodiment, a luer cap 24 comprising a resilient well-shaped cylinder attaches by a band 25 to an o-ring 26 received on the barrel 12. In a preferred embodiment, the o-ring 26 seats in a groove or channel that extends around the circumference of the barrel 12. In an alternate embodiment, the luer cap 24 is provided in a syringe kit as a separate loose component.

A plunger rod 28 extends into the open end 14 of the barrel 12. A plunger body 29 attaches to the end of the plunger rod 28 that inserts into the barrel 12. A preferred plunger body is disclosed in U.S. Pat. No. 5,377,689. The plunger body facilitates drawing the sample of blood and seals the sample from communication, for example, with the atmosphere, to prevent contamination and spilling of the sample from the syringe.

A needle assembly 30 is shown in FIG. 2 exploded from the barrel 12. The needle assembly 30 includes a metal canula or needle 16 having a beveled tip 32 for piercing tissues for taking samples of blood from patients or communicating fluids to patients. The needle 16 is held by a hub 34 which comprises a tube 35 open at one end 36 for receiving the luer 20 and closed at the other end 37 for holding the needle 16. Typically, the needle 16 is secured in the hub 34 with an epoxy. The base of the hub 34 has wings 38 that extend outwardly for threadingly engaging the threaded shroud 22.

An enclosing device 40 slip-fit attaches to the shroud 22 at the end 18 of the barrel 12. The enclosing device comprises a base 42, a sheath 44, and a cup-shaped cap 46 that defines an opening 48 through which the needle 16 extends coaxially. Flanges 50 extend laterally from opposite sides of a lower portion of the cup-shaped cap The sheath 44 comprises a tube that is extendable from a retracted position to and extended position. The sheath 44 is preferably formed of a woven or braided fibers, including metal wires, plastic strands, rubber, or other materials that can be woven or braided for forming a mesh-like tube. A 100 mesh 0.005 inch wire tubular braid of ⅜ inch diameter readily compacts to about ⅛ inch length in a retracted position and extends to about 2 inches in an extended position. In an alternate embodiment, the sheath 44 is a plastic tube with accordion-style folds for compressing the sheath to a retracted position and unfolding to an extended position.

The respective ends of the sheath 44 attach to the base 42 and the cap 46. In the illustrated embodiment, the base 42 has a series of tabs 51 that angle outwardly for grippingly engaging the sheath 44. In an alternate embodiment, the base 42 is adhered to the sheath 44, such as by sonic welding or with an adhesive, depending on the material used in the sheath. An upper surface of the cap 46 includes the opening 48 through which the needle 16 extends for use of the syringe 10, as discussed below. A resilient washer-like pad 52 is secured to an interior surface of the cap 46 for a purpose discussed below. A conventional needle cap 54 is illustrated exploded from the enclosing device 40. The needle cap 54 is supplied on the needle 16 and is discarded prior to use of the syringe 10.

The needle assembly 30 is disposed coaxial within the enclosing device 40 to form a unitary part that is installed and removed as a unit. An upper portion of the interior of the base 42 is sized for receiving the hub 34 which press-fits therein for being held within the enclosing device 40. With respect to FIG. 2, the lower portion of the base 42 slip fits around the shroud 22 when the needle assembly 30 is connected to the barrel 12. This is accomplished by gripping the base 42 and rotating the base in alignment with the shroud 20. The wings 38 engage the thread of the shroud 22, thereby connecting the hub 34 to the shroud. The tube 35 matingly receives the luer 20 for communicating fluids between the needle 16 and the barrel 12.

FIGS. 3A–3D show a sequence of steps for using the enclosing device 40 with the syringe 10. The needle assembly 30 is inserted coaxially into the enclosing device 40. The hub 34 is then threadingly engaged to the shroud 22 by screwing the wings 38 into the thread of the shroud. The hub 34 thereby seats into the well between the luer 20 and the shroud 22 while the base 42 slippingly engages the exterior of the shroud. The needle cap 54 extends coaxially through the opening 48 in the cap 46. The sheath 44 bunches together between the base 42 and the cap 46 near the end 18 in a retracted position. In one embodiment, the sheath 44 is formed of a plastic having a "memory" which biases the sheath in a compressed or retracted position. The syringe 10 with the enclosing device 40 disposed in a retracted position is ready of wrapping and sterilization, shipping, and use.

For use, the needle cap 54 is removed from the needle 16, leaving the needle extending outwardly of the opening 48 in the cap 46 of the enclosing device 40, as illustrated in FIG. 3A. The woven sheath 44 remains bunched between the base 42 and the cap 46 near the end 18.

Figure 3B:
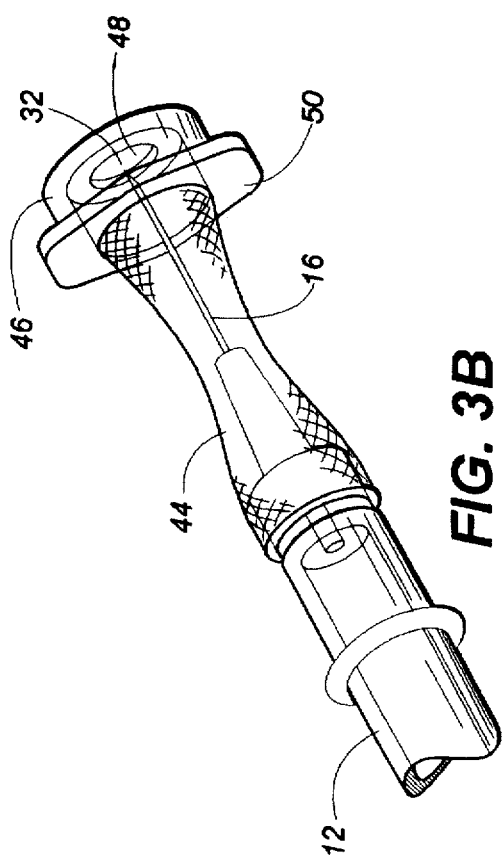
Figure 3C:
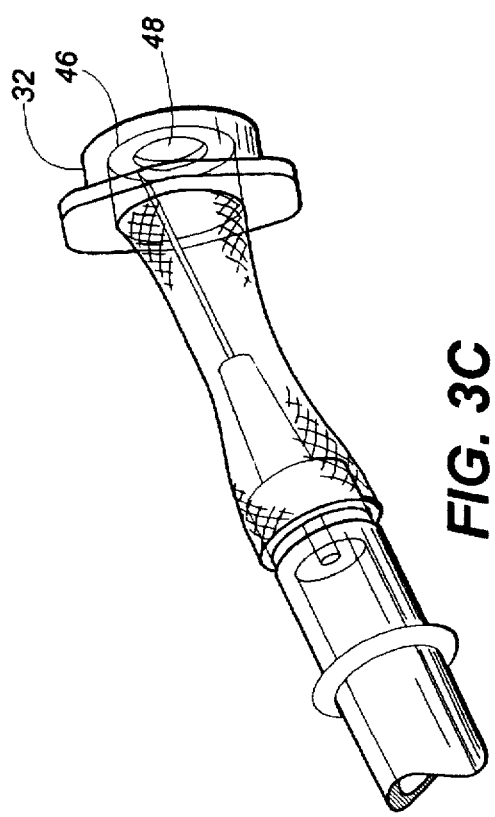

With reference to FIG. 3B, after the syringe 10 is used (for delivering medication to a patient or for obtaining a sample of bodily fluid), the sheath 44 of the enclosing device 40 is extended longitudinally outwardly to cover the syringe. The cap 46 is pulled longitudinally away from the barrel 12 to extend the sheath 44 over the needle 16 until the tip 32 of the needle is within the sheath. This is preferably accomplished by hooking one of the flanges 50 on an edge of a table or other sturdy fixture and pulling the syringe barrel 12 longitudinally away from the cap 46. This causes the cap 46 to move to an extended position relative to the needle 16. With reference to FIG. 3C, the barrel 12 is then moved laterally relative to a longitudinal axis defined by the needle 16 in order to move the opening 48 of the cap 46 away from the tip 32 of the needle 16, thereby bringing an interior surface of the sheath 44 near the needle tip.

Figure 3D:
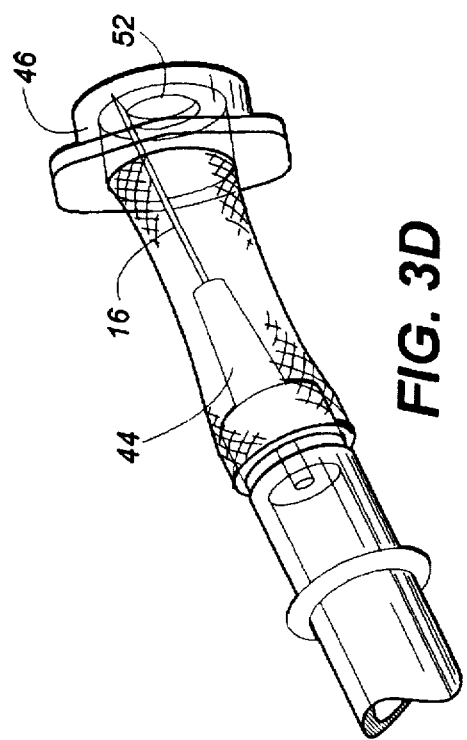

With reference to FIG. 3D, the cap 46 is then moved longitudinally from the extended position to an intermediate position with the tip 32 of the needle 16 engaged with the interior surface of the cap. In this engaged intermediate position, the sheath preferably induces a biasing pressure against the needle 16, thereby holding the needle and the cap from inadvertent separation due to bumping or other incidental contacts. In a preferred embodiment, the tip 32 of the needle 16 enters into the resilient pad 52 which preferably includes a hydrophilic gelatin that absorbs some of the bodily fluids from the needle and solidifies to seal the needle. The resilient pad 52 also resists lateral movement of the needle 16 relative the cap 46, in the event the enclosing device 40 is bumped or contacted, thereby preventing the needle tip 34 from extending inadvertently through the opening 48 in the cap.

The needle assembly 30 and the enclosing device 40 may then be removed as a unitary piece for disposal of the needle 16. The base 42 is grasped and rotated, thereby unscrewing the hub 34 from the shroud 22. This disconnects the needle 16 from the barrel 12. The needle assembly 30 covered by the enclosing device 40 is then placed in a sharps container for disposal. The luer 20 is then closed by causing the cap 24 to become inverted on a table with an open end upward. The syringe 10 is oriented with the luer 20 towards the cap 24 and thereafter moved to insert the luer into the cap.

FIG. 4 illustrates a surgical tool 60 having a handle 61 with a connector 62 at one end for engaging a coupler of a cutting tool 66, such as the surgical scalpel having a cutting blade 67. In the illustrated embodiment, the connector 62 comprises an open-ended cylinder extending coaxially from the handle 61, similar to the shroud 22. The interior surface of the connector 62 is threaded. The coupler 64 includes wings 68 that extend laterally for threadingly engaging the threaded connector 62.

For use, the tool 66 is disposed coaxially within the enclosing device 40. The base 42 receives the coupler 64 with a press-fit engagement. The unitary assembly of the tool 66 and the enclosing device 40 is then attached to the handle 61. The coupler 64 is grasped and rotated in contact with the connector 62. The wings 68 threadingly engage the connector 62 and the base 42 of the enclosing device 40 slip fits onto the connector. The cap 46 is disposed in a retracted position for exposing the cutting blade 67 for use of the tool 60, whereby the sheath bunches together adjacent the connector 62.

After use of the cutting tool, the flanges 50 of the cap 46 are caught on an edge of a table and the handle 62 pulled longitudinally away. This causes the sheath 44 to move from the retracted, bunched position to an extended position with the tip of the tool 66 within the cap The handle 62 is then moved laterally relative the longitudinal axis of the tool 60 in order to bring a surface of the sheath 44 near the tip of the tool 66. The handle 62 is then moved longitudinally inward to cause the tip of the tool 66 to engage with the cap The surgical tool 66 is thereafter separated from the handle 62 by unscrewing the tool 66 and the enclosing device 40 as a unitary member. The base 42 of the enclosing device 40 is grasped and rotated, causing the wings 68 of the coupler 64 to unscrew from the connector 62. The enclosing device 40 remains connected to the coupler 64, and the enclosed tool 66 is deposited in a sharps container for disposal. The handle 61 may then be sterilized and re-used. In an alternate embodiment, the handle 61 and the tool 66 are integrally formed, whereby the entire tool 60 is placed in the sharps container for disposed following use and covering by the sheath 44 of the enclosing device 40.

FIG. 5 illustrates an alternate embodiment 70 of the present invention. The barrel 12 of the sampling syringe 10 or handle 62 includes three channels 72 extending longitudinally on an exterior surface. The channels 72 are preferably equally spaced around the circumference of the barrel 12. Arms 74 extend longitudinally from the end 18 of the barrel 12 in alignment with the channels 70. A stop 76 is defined at the respective distal end of the arms 74. A series of slots 78 are defined in the channels 72 and the arms 74 for a purpose discussed below. A tube 80 slidingly extends over the barrel 12. Three blocks 82 configured for engaging the channels 72 extend radially from an inner surface of the tube 80 at a first end. A tongue or plate 84 extends from each of the blocks 82 at an acute angle relative to the end 18. The tongues 84 engage the slots 78 as the tube 80 is moved from a recessed position with the arms 74 exposed to an extended position with the arms covered. In the extended position, the tube 80 covers a surgical tool such as the needle assembly 30 held in the shroud 22 discussed above. The reverse orientation of the tongues 84 relative to the extendable movement of the tube 80 and the engagement of the plates 84 in the slots 78 prevent the tube from inadvertent reverse movement which would expose the tip 32 of the needle.

FIG. 6 illustrates the sampling syringe 10 of FIG. 1 with a flexible plug 90 that is insertingly received in the luer 20. The plug 90 in the illustrated embodiment has a cylindrical body 92 with a lip 94 extending radially outwardly at one end. The plug 90 inserts into the luer 20 to block communication with the barrel 12. The lip 94 extends radially outwardly of the luer 20 and prevents the plug 90 from being pushed through the luer into the barrel 12 during installation of the needle assembly 30.

In this embodiment, the needle 16 is disposed in the hub 34 so that a portion 96 extends coaxially into an interior 98 of the hub 34. As the hub 34 threadingly engages the shroud 22, an inner tip 99 of the needle 16 pierces through the plug 90. The inner tip 99 extends through the body 92 for communication between the needle 16 and the barrel 12. The base 42 of the enclosing device 40 slip-fits over the shroud 22 as discussed above.

After the syringe is used, for example, for drawing a sample of bodily fluids from a patient, the needle assembly 30 and the enclosing device 22 are removed as a unitary member and discarded as discussed above. This is accomplished by unscrewing the hub 34 from engagement with the threaded shroud 22. This extracts the needle 16 from the plug 90. The body 92 closes the opening in the plug 90 formed by the needle 16 to resist leakage of fluids from the barrel 12. The body 92 is preferably made of a resilient material and can include a hydrophilic gelatin for sealingly closing the opening made by the needle 16, thereby preventing release of the fluid sample in the barrel or contamination thereof by the atmosphere.

FIG. 7A is an exploded prospective view of an alternate embodiment of the present invention that includes an intermediate connector 100 mounted between the barrel 12 and the needle assembly 30. The connector 100 best illustrated in side plan view in FIG. 7B has a central tube 102 with a lower base portion 104 having wings 106 extending laterally outward. An upper portion 108 includes a cylindrical shroud 110 with a threaded interior surface. In the embodiment illustrated in FIG. 7A, U-shaped slide guides 114 extend from the sides of the shroud, equally spaced apart on the surface of the shroud. The guides 114 have lateral walls 116 connected by a spaced-apart pair of bands 118 that define a gap 120, for a purpose discussed below.

In the illustrated embodiment, a tripod-shaped closure device 130 is received by the intermediate connector 100. The closure device has three arms 132 that extend from an edge 134 of a cup-shaped cap 136. A dish-shaped surface 138 at the other end of the cap 136 defines an opening 140 for receiving therethrough the needle 16 and the conventional needle cap 54. The surface 138 tapers at a slight slope towards the edge 134. A washer-like pad 142 is secured to the inside walls of the cap. In an alternate embodiment (not illustrated), the cap 136 has a single arm 132 that is received by the slide guide 114 on the intermediate connector.

The arms 132 each have an aligned series of saw tooth projections 144 on an exterior face. Each arm 132 has a distal end 146 that angles outwardly to define a stop. In operation, the intermediate member 100 is threadingly received on the barrel 12. The wings 106 engage the threads of the shroud 22. The tube 102 matingly engages the luer 20 as the wings 106 thread onto the shroud 22. The needle cap 54 is positioned over the needle 16 on the needle assembly 30 which is then attached to the intermediate connector 100 by screwing the wings 38 into the threaded shroud 110.

The closure device 130 is then installed. The stops 146 on the arms 132 are bent temporarily into substantial longitudinal alignment with the arms and pushed through the respective slide guides 114. The capped needle 16 extends through the opening 140 of the cap 136 as the closure device 130 is moved to a retracted position with the cap near the intermediate member 100. As illustrated in FIG. 8A, the cap 54 is removed to expose the needle 16 for use of the syringe 10. After use, the closure device 130 is moved outwardly to an extended position relative the tip 34 of the needle 16. The stops 146 prevent the closure device 130 from readily being removed from the intermediate connector 100 as the device is moved to the extend position.

With respect to FIG. 8B, the closure device 130 is then moved laterally with respect to longitudinal axis of the syringe 10 in order to bring the tip 32 of the needle 16 adjacent an inner wall of the cap 136. The closure device 130 is then retracted slightly to embed the tip 32 of the needle 16 in the pad 142 on the inside of the cap. The needle 16 is then secured from inadvertent contact by nurses, patients, and others. The needle is then removed for disposal in a sharps container by unscrewing the intermediate connector 100 from the shroud 22 of the syringe 10. The luer 20 is then closed by the cap 24.

It is noted that an alternate embodiment of the intermediate member 100 is gainfully used with the enclosing device 40 illustrated in FIGS. 1 and 2. This alternate embodiment does not include the slide guides 114. The enclosing device 40 attaches to the shroud 110 and the lower base portion 104 connects to the shroud 22 of the syringe 10.

FIG. 9 is a prospective view of an alternate embodiment of a needle protection device 170 for the syringe 10. The device 170 comprises a unitary assembly having a ring 173 for being slidingly received on the tubular base of the intermediate connector 100. The inner diameter of the ring 173 is slightly larger then the outer diameter of the tubular base of the intermediate connector 100 for being press fit thereon while allowing the ring to rotate around the circumference as discussed below. A lever 176 connects by a flexible hinge 178 to the ring 172. An arm 184 extends laterally from the lever 176 intermediate the ring 172 and a distal end 182. The arm 184 joins the lever 176 by a flexible living hinge 181. The arm 184 has a lower portion or link 180 connected by a living hinge 186 to a main portion 183 of the arm, for a purpose discussed below. The length of the link 180 is relatively shorter than the main portion 183. A distal end of the arm 184 defines an inverted bowl-shaped cap 188 having a resilient pad 190. A C-shaped clip 192 extends from the arm 184 between the hinge 186 and the cap 188. The clip 192 has a diameter sized for grippingly engaging the barrel 12 of the syringe 10.

The device 170 is used in cooperation with the intermediate connector 100. The ring 173 slip fits on the tubular base of the intermediate connector 100 which is then threadingly connected to the shroud 22 by engaging the wings 106 to the shroud. The needle assembly 30 closed by the cap 54 is threadingly engaged to the cylindrical shroud 110 of the intermediate connector 100. The arm 184 pivots by the flexible hinges 181 and 186 with the short link 180 enabling the arm 184 to pivot to a parallel position relative the body 12 of the syringe 10. This brings the C-clip 192 into engagement with the barrel 12 of the syringe 10, for the syringe to be used with the needle protective device 170 secured to the barrel. It is preferred during use that the bevel of the tapered tip 32 face away from the skin of the patient so that the user may observe the needle for proper insertion. Because the canula or needle 16 is fixed at a random orientation to the hub 34 of the needle assembly 30, it can be that the arm 184 is in an interfering position for properly using the syringe 10. In such instance, the device 170 is rotated around the axis of the barrel 12 which moves freely by the ring 172 and the C-clip 192 turning with respect to the barrel.

After the syringe 10 is used, the cap 188 is positioned over the tip 34 of the needle to secure it from inadvertent contact. The C-clip 192 is disengaged from the barrel 12 and the arm 184 pivoted toward the needle 16 to position the cap 188 outwardly of the needle tip 32. With the syringe 10 held in one hand, the thumb of the user bears on the lever 176 pushing it towards the barrel 12. The lever 176 pivots at the hinge 178 and the movement of the lever 176 away from the tip 32 causes the arm 184 to move inwardly toward the intermediate connector 100 and away from the tip 32, thereby bringing the cap 188 into alignment with the needle 16. The user continues to push the lever 176, thereby causing the arm 184 to pivot at the hinge 186 and flex inwardly. This brings the cap 188 into contact with the tip 32 of the needle 16 and embeds the tip in the resilient pad 190. The needle 16 may then be disconnected for disposal by unscrewing the connector 100 from the shroud 22 and separated for disposed as a single unit in a sharps container.

FIG. 10A is a perspective view of a capping device 200 for covering a tip end 32 of a cutting surface, such as the syringe needle 16, of a surgical instrument, such as a sampling syringe 10. The capping device 200 comprises an elastic elongate member 202 that attaches to the sampling syringe 10 near the end 18 to which the needle assembly 30 attaches. It is appreciated from the discussion above that the needle assembly 30 attaches either directly to the shroud 22 or to the intermediate member 100 which connects to the shroud as shown in the illustrated embodiment. An anchor block 204 secures an end of the elongate member 202 to the intermediate member 100. The elongate member 202 can be made of spring wire or flexible plastic. In one embodiment, the anchor block 204 comprises a U-shaped projection on the exterior surface for receiving an end of the spring wire elongate member. The end of the spring wire slips into the gap between the anchor block 204 and the surface of the intermediate member 100. In the embodiment with a flexible plastic member, the anchor block 204 and the elongate member 202 are preferably molded integral with the intermediate member 100.

A bowl-shaped cap 206 attaches to a distal end of the elongate member 202. The cap 206 is sufficiently hard to resist piercing by a sharp cutting edge, such as the tip 32 of a needle 16. In the illustrated embodiment, the cap 206 defines an interior space that is filled with a resilient material 208. A surface 210 defines a narrow slot 212 having a width slightly less than the diameter of the needle 16 or the tip portion of a blade-like cutter.

FIG. 10B illustrates an enlarged side plan view of a portion of the capping device 200 to illustrate a retaining block 214 extends outwardly from the intermediate member 100 and is spaced-apart from the anchor block 204. The retaining block 214 releasably retains the elongate member 202 by engaging an intermediate portion thereof and holding the elongate member in a retracted position away from the cutting surface means. The elongate member 202 flexibly bends in order to engage the retaining block 214 which is substantially L-shaped to define a gap 216 between a lower surface of the block and the exterior surface of the intermediate member 100. The L-shaped block 214 is orientated in alignment with a transverse plane 215 for inserting and holding the elongate member 202. A hook 218 depends from the lower surface and extends towards the intermediate member 100. The elongate member 202 slides through the gap 216 and a side edge of the elongate member engages the hook 218 which restricts the elongate member from egress.

After the sampling syringe 10 is used, the capping device is moved to cover the tip 32 of the needle 16. The elongate member 202 is pressed inwardly towards the intermediate member 100 to disengage the elongate member from the hook 218. The elongate member 202 is then slidingly moved out of the gap 216. Upon release, the elongate member 202 springs outwardly into an extended position substantially parallel to the needle 16, with the cap 206 positioned outwardly of the tip 32. The sampling syringe 10 is then moved forcibly against a fixed surface to bear the needle 16 into the cap 206. This causes the tip 32 to enter through the slot 212 and be received by the resilient material in the cap 206. The inward force causes the surface 210 to taper inwardly biased against the needle 16 in the slot 212. The edges of the surface at the slot 212 bear forcibly against the needle 16 and resist removal or detachment of the needle from the cap.

The intermediate member 100 with the needle assembly 30 and the capped needle 16 then is removed from the syringe 10 as discussed above for disposal in a sharps container.

FIG. 11A illustrates a needle enclosing device 230 attached to the intermediate member 100 for engagement with the sampling syringe 10 having the needle 16 in a needle assembly 30. The device 230 has a plate 232 that attaches to the intermediate member 100. In a preferred embodiment, the device 230 is molded integral with the intermediate member. In an alternate embodiment (not illustrated), a ring attaches to a bottom surface of the plate 232 and is received by a portion of the intermediate member to secure the device 230 thereto. The ring slip-fits to the intermediate member 100 to facilitate rotation of the device 230 around the axis of the syringe 10, so that the device does not interfere with positioning the needle in a patient.

A pair of spaced-apart guide posts 234 extend laterally from the plate 232 at a first end. A stop 236 at the distal end of each post 234 extends towards the opposing arm, for a purpose discussed below. A second end of the plate 232 terminates in a reversed U-shape hook 238. A lever arm 240 attaches with a living hinge 242 to an upper surface of the plate 232. A thumb grate 244 defines a textured surface on a portion of the lever arm 240 which angles outwardly. A pair of fingers 245 extend laterally from near a distal end of the thumb grate 244.

An arm 246 attaches to the lever arm 240 with a living hinge 248 intermediate the hinge 242 and the fingers 245 of the lever arm. The arm 246 has a bend 252 which defines two portions 254 and 256. The portion 254 is removably received between the fingers 245. A distal end of the arm 246 defines a cap 257 having an opening 258 into an interior space for receiving the tip end 32 of the needle 16.

With reference to FIGS. 11A and 11B, a locking plate 260 attaches with a living hinge 262 to a lower edge of the lever arm 240. A connector arm 264 extends between a lower surface of the locking plate 260 and an inside surface of the plate 232 near the living hinge 242. The connector arm 264 restricts outward pivoting of the locking plate 260 and facilities the relative longitudinal movement of the locking plate, as discussed below. A recessed slot 266 in the plate 232 receives the connector arm 264. A distal end 268 of the locking plate 260 is received in the hook 238 of the plate 232.

The operation of the needle enclosing device 230 is described with reference to FIGS. 11A–11D. The device 230 is placed in an retracted position as illustrated in FIG. 11A with the arm 246 held by friction-fit between the fingers 245. The needle assembly 30 attaches to the luer of the intermediate member 100. The syringe 10 is then used for delivering a solution or extracting a sample from a patient. In a preferred embodiment, the lower portion 104 of the intermediate member 100 slip-fits over the luer 20 of the syringe 10. The device 230 thereby readily rotates around a longitudinal axis of the syringe, in the event the device interferes with the proper positioning of the needle into the patient.

After use of the syringe 10, the needle 16 is capped with the protection device 230. The user's thumb bears against a backside of the arm 246 near the upper surface of the locking plate 260. The user pushes the arm 246 from between the fingers 245 and also pushes the lever arm 240 forward to extract the distal end 268 of the locking plate 260 from the hook 238. As illustrated in FIG. 11B, the arm 246 pivots towards the tip 32 of the needle and the locking plate 260 moves outwardly and longitudinally relative the plate 230. The arm 246 is then pushed past the stops 236 between the posts 234. The lever arm 240 continues to pivot forwardly and the posts 234 guide the longitudinal travel of the arm relative the needle 16 to position the device 230 in an extended position with the cap 257 outwardly of the tip 32, as illustrated in FIG. 11C. The stops 236 restrict inadvertent removal of the elongate member from between the guide posts.

The user then pushes in a reverse direction on the thumb grate 244 to move the device 230 into an intermediate position which brings the tip 32 of the needle 16 into enclosing contact with the cap 257. The locking plate 260 is simultaneously moved longitudinally in a reverse direction and inwardly towards the plate 232 to re-engage the distal end 268 with the hook 238. The enclosing device is thereby locked into the intermediate position with the needle tip 16 enclosed in the cap 257. The reciprocating action of the lever arm 240 in advancing the cap 257 outwardly of the tip 32 and retracting the cap for receiving the tip, together with the depth of the cap, facilitates using the protective device 230 with syringes having common, presently marketed needle lengths. In a preferred embodiment, the cap includes a resilient material for securing the tip 32. In an alternate embodiment, the cap 257 includes a slotted surface through which the needle 16 extends. The edges of the slot flex inwardly as the needle 16 is pushed through and bear against the needle to restrict removal. The intermediate member 100 is thereafter disengaged from the syringe 10 for disposal in a sharps container.

FIG. 12A illustrates an alternate embodiment 330 of the needle enclosing device 230 illustrated in FIG. 11A discussed above. In this embodiment, the arm 246 is releasably secured in position by interlocking means having matingly engaging surfaces. The plate 232 is shortened and the locking plate 260 and the hook 238 are not included. The illustrated embodiment uses interlocking bores and pegs. A bore 270 is defined in a lower portion 254 of the arm 246. A peg 272 extends upwardly from the lever arm 240 in axial relationship with the bore 270, such that the peg enters the bore when the arm 246 is folded on the living hinge 242 into contact with the lever arm, as discussed below. The peg 272 includes an annular skirt 274 for creating an interference fit within the bore 270 to lock the arm 246 to the lever arm 240. As illustrated in FIG. 12B, a second peg 276 extends from a lower surface of the lever arm 240 coaxially with a bore 278 defined in the plate 232. The peg 276 clip fits in the bore to assist securing the arm 246 in a retracted position between the fingers 245. In an alternate embodiment (not illustrated), the interlocking means comprises relatively engaging surfaces of a lip on the lever arm 240 engaging a groove in the plate 232. Other interlocking means may be gainfully used to secure the arm 246.

The operation of the needle enclosing device 230 is described with reference to FIGS. 12A–12D. The device 230 is placed in an retracted position as illustrated in FIG. 12A with the arm 246 held by friction-fit between the fingers 245. The syringe 10 is then used for delivering a solution or extracting a sample from a patient.

After use of the syringe 10, the needle 16 is capped with the protection device 230. The user's thumb bears against a backside of the lever arm 240 and the arm 246. The user pushes the arm 246 from between the fingers 245 and pushes the lever arm 240 upwardly to extract the peg 276 from the bore 278. This allows the arm 246 to move longitudinally relative the needle 16 and pivot on the living hinge 248. The arm 246 is free relative the lever arm 240 and the plate 232. As illustrated in FIG. 12B, the arm 246 pivots towards the tip 32 of the needle as the lever arm 240 pivotingly moves towards the tip 32 of the needle 16. The arm 246 is then pushed past the stops 236 between the posts 234 and the lever arm 240 continues to pivot forwardly. The posts 234 guide the longitudinal travel of the arm relative the needle 16 to position the device 230 in an extended position with the cap 257 outwardly of the tip 32, as illustrated in FIG. 12C.

The user then pushes in a reverse direction on the thumb grate 244 to move the device 230 into an intermediate position. This brings the tip 32 of the needle 16 into enclosing contact with the cap 257. The peg 272 engages the bore 274 to lock the arm 246 to the lever arm 240 as the lever arm moves in a reverse direction to re-engage the peg 276 in the bore 278. The pegs 272 and 276 and bores 274 and 278 respectively cooperate to lock the device 230 in the extended position enclosing the tip 32 of the needle 16 in the cap 257. In a preferred embodiment, the cap includes a resilient material for securing the tip 32. In an alternate embodiment, the cap 257 includes a slotted surface through which the needle 16 extends. The edges of the slot flex inwardly as the needle 16 is pushed through and bear against the needle to restrict removal. The intermediate member 100 is thereafter disengaged from the syringe 10 for disposal in a sharps container.

The foregoing has disclosed an improved enclosing device for securing cutting surfaces of surgical instruments from inadvertent contact by persons using such instruments or being near them during handling, use, or disposal. While most of the disclosed embodiments illustrate capping of needles on sampling syringes, these safety enclosing devices are readily applied to other surgical instruments having cutting surface means such as scalpels. It should be understood therefore that the above described embodiments merely illustrate principles of the invention in preferred forms. Many modifications, additions, and deletions may, of course, be made thereto without departure from the spirit and scope of the invention as set forth in the following claims.

What is claimed is:

1. A sampling syringe with a closure device for capping a needle attached to the syringe, comprising:

an elongated barrel open on a first end and a needle attached by a hub at a second end for communication with the barrel;

a plunger rod with a plunger body attached at a first end slidably insertable into the open first end of the barrel;

a unitary closing device comprising:
a ring sized for being engaged to a tubular portion of the hub;
a lever hingedly attached to the ring;
a link member hingedly connected to the lever intermediate the ring and a distal end of the lever;
an arm connected by a flexible hinge to the link and having a dish-shaped cap member at a distal end,
the arm pivotable to a position in substantial parallel alignment with the needle whereby the cap member is outwardly of the tip of the needle and the cap member being brought into engagement with the tip of the needle by moving the lever towards the open end of the barrel.

2. The sampling syringe as recited in claim 1, further comprising a C-shaped clip attached to the arm for securing the arm to the barrel pending usage of the closure device for capping a needle.

3. A needle enclosing device for capping a tip of a syringe needle after use, comprising:

a plate having a pair of spaced-apart guide posts extending laterally at a first end of the plate;

means for attaching the plate to a sampling syringe;

a lever arm pivotally connected at a first end to an upper surface of the plate away from the guide posts, a distal end of the lever arm having a pair of spaced-apart fingers extending laterally therefrom, the lever arm pivotable between a back position and a forward position;

an elongate arm pivotally connected at a first end to an upper surface of the lever arm medial the connection thereof to the plate and the distal end of the lever arm, a cap at a distal end of the elongated arm for receiving a tip end of a needle in fluidal communication with a barrel of the sampling syringe, the elongate arm pivotable from a retracted position with the arm held between the fingers and an extended position with the arm held between the guide posts;

means for releasably securing the lever arm in the back position, whereby the elongate arm, being released from between the fingers, pivots from the retracted position to the extended position while the lever arm is moved from the back position to the forward position to dispose the cap outwardly of the tip of the needle and the lever arm, being then moved to the back position, causes the elongate arm to move to an intermediate position for engaging the tip of the needle in the cap.

4. The needle enclosing device as recited in claim 3, wherein the means for releasably securing comprises:

a distal end of the plate terminating in a U-shaped hook opening towards the lever arm;

a locking plate pivotally connected to a lower surface of the lever arm intermediate the connection of the lever arm to the plate and the distal end of the lever arm, a distal end of the locking plate removably received by the hook for securing the lever arm in the back position.

5. The needle enclosing device as recited in claim 3, wherein the means for releasably securing comprises:

the plate defining a bore in an upper surface and spaced from the connection of the lever arm in a direction away from the guide posts;

a peg extending laterally from a lower surface of the lever arm for coaxial engagement with the bore when the lever arm is in the back position.

6. The needle enclosing device as recited in claim 5, further comprising:

the lever arm defining a second bore in an upper surface;

a second peg projecting upwardly from the plate intermediate the guide posts and the connection of the lever arm thereto, the second peg disposed for coaxial engagement with the second bore upon pivoting the elongate arm from the retracted position to the extended position, whereby the engagement of the second peg and the second bore secure the elongate arm to the lever arm.

* * * * *